US012599644B2

(12) United States Patent
Ma et al.

(10) Patent No.: US 12,599,644 B2
(45) Date of Patent: Apr. 14, 2026

(54) TREATMENT OF CORONAVIRUS INFECTION WITH Flt3 RECEPTOR INTERACTING LECTIN (FRIL)

(71) Applicant: Academia Sinica, Taipei (TW)

(72) Inventors: Che Ma, Taipei (TW); Jia-Tsrong Jan, New Taipei City (TW)

(73) Assignee: Academia Sinica, Taipei (TW)

( * ) Notice: Subject to any disclaimer, the term of this patent is extended or adjusted under 35 U.S.C. 154(b) by 741 days.

(21) Appl. No.: 17/922,977

(22) PCT Filed: May 6, 2021

(86) PCT No.: PCT/US2021/030994

§ 371 (c)(1),
(2) Date: Nov. 3, 2022

(87) PCT Pub. No.: WO2021/226294

PCT Pub. Date: Nov. 11, 2021

(65) Prior Publication Data

US 2023/0346872 A1 Nov. 2, 2023

Related U.S. Application Data

(60) Provisional application No. 63/021,648, filed on May 7, 2020.

(51) Int. Cl.
*A61K 36/896* (2006.01)
*A61K 45/06* (2006.01)
*A61P 31/14* (2006.01)

(52) U.S. Cl.
CPC ............ *A61K 36/896* (2013.01); *A61K 45/06* (2013.01); *A61P 31/14* (2018.01)

(58) Field of Classification Search
None
See application file for complete search history.

(56) References Cited

U.S. PATENT DOCUMENTS 4,742,046 A * 5/1988 Bliah ..................... C07K 14/42
530/370

FOREIGN PATENT DOCUMENTS

WO WO 2006/110577 * 10/2006 ............. A61P 37/06
WO WO 2020/051397 * 3/2020 ............. C07K 14/42

OTHER PUBLICATIONS

Liu et al., Cell Reports 32, 108016; Aug. 11, 2020: https://doi.org/10.1016/j.celrep.2020.108016 (Year: 2020).*
Bhattacharya et al., PLoS ONE 12(3): e0171355. https://doi.org/10.1371/journal.pone.0171355; 22 pages total (Year: 2017).*
Fenton et al., Medicinal Chemistry Research (2020) 29:1133-1146) (Year: 2020).*
Pucci et al., Current Opinion in Structural Biology 2022, 72: 161-168 (Year: 2022).*
Pak et al., PLoS ONE 18(3): e0282689. https://doi.org/10.1371/journal.pone.0282689 (Year: 2023).*
Chris A. Silagy & Katrina Campion, Annals of Medicine, 31:5, 313-317, DOI: 10.3109/07853899908995897 (Year: 1999).*

* cited by examiner

*Primary Examiner* — Christina M Borgeest
(74) *Attorney, Agent, or Firm* — NZ Carr Law Office

(57) ABSTRACT

Disclosed herein is a method for treating or preventing a coronavirus infection, which comprises administering to a subject in need thereof an effective amount of a composition comprising Flt3 receptor interacting lectin (FRIL) from *Lablab purpureus*. Also disclosed is a pharmaceutical composition comprising a pharmaceutically acceptable excipient, a *Lablab purpureus* FRIL, and an additional therapeutic agent.

13 Claims, 2 Drawing Sheets

Specification includes a Sequence Listing.

TREATMENT OF CORONAVIRUS INFECTION WITH Flt3 RECEPTOR INTERACTING LECTIN (FRIL)

CROSS-REFERENCE TO RELATED APPLICATION

This application is a U.S. National Stage Filing under 35 U.S.C. 371 from International Patent Application Serial No. PCT/US2021/030994, entitled "TREATMENT AND PRE-VENTION OF CORONAVIRUS INFECTION," filed on May 6, 2021, and published on Nov. 11, 2021, which claims the benefit of U.S. Provisional Application No. 63/021,648, filed on May 7, 2020; the disclosure of which are incorporated by reference herein in their entireties.

BACKGROUND OF THE INVENTION

1. Field of the Invention

The present disclosure relates to a treatment of virus infection. More particularly, the disclosure invention relates to the treatment and prevention of coronavirus infection.

2. Description of Related Art

The ongoing pandemic of COVID-19, caused by the emergence of the Severe Acute Respiratory Syndrome coronavirus 2 (SARS-CoV-2) has led to a worldwide outbreak, and resulted in more than a million infections and tens of thousands of deaths. To date, no specific medical treatments or vaccines for COVID-19 have been approved (WHO coronavirus disease (COVID-2019) situation reports-105).

Lectins recognize unique glycans displayed on glycoproteins. Lectins from various sources have been shown to exhibit potent antiviral properties by inhibiting infection of clinically important viral pathogens. Several lectins have been identified as potential therapeutic agents in the prevention of viral transmission in human immunodeficiency virus (HIV) and coronaviruses (SARS-CoV and MERS-CoV) [Mitchell, C. et al. Antiviral Res. 2017]. However, there is no lectin, particularly plant lectin, that has been reported to be effective for treating and preventing SARS-CoV-2 infection.

WO2020051397 discloses that Flt3 receptor interacting lectin (FRIL) from *Lablab purpureus* is effective against influenza virus infection. No specific activity of *Lablab purpureus* FRIL against coronavirus infection, particularly SARS-CoV-2 infection, was reported.

There is an urgent need to find effective ways of dealing with the health crisis caused by SARS-CoV-2. Novel drugs and approaches for effective treatment and prevention of the emerging coronavirus infection in humans is highly desired.

SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on the unexpected finding that an Flt3 receptor interacting lectin (FRIL) protein from *Lablab purpureus* exhibits an effective activity for inhibiting and neutralizing SARS-CoV-2, thus providing a means of treating and/or preventing the emerging coronavirus infection in humans. This is the first report that a plant lectin (e.g. *Lablab purpureus* FRIL) displays an antiviral activity that can effectively neutralize SARS-CoV-2. The finding indicates that *Lablab purpureus* FRIL can serve as a neutralization agent against the emerging coronavirus.

Accordingly, the present invention provides a method for treating or preventing coronavirus infection, the method comprising administering to a subject (e.g., a mammal) in need thereof an effective amount of an Flt3 receptor interacting lectin (FRIL) or a composition comprising the same. As described herein, the FRIL is a *Lablab purpureus* FRIL. The coronavirus described herein includes SARS-CoV-2, and may include severe acute respiratory syndrome coronavirus (SARS-CoV) and Middle East respiratory syndrome coronavirus (MERS-CoV). In preferred embodiments, the coronavirus infection is caused by SARS-CoV-2.

In certain embodiments, the FRIL comprises an amino acid sequence of SEQ ID No:1, or an amino acid sequence that is substantially identical to SEQ ID NO:1.In certain embodiments, the FRIL comprises a FRIL polypeptide in a cleaved form (removal of a loop domain). Specifically, a cleaved form of FRIL includes a N-terminal domain (beta subunit, e.g. SEQ ID NO: 2) and a C-terminal domain (alpha subunit, e.g. SEQ ID NO: 3). In some embodiments, the beta subunit and the alpha subunit are associated to form a monomer; further, two units of such monomer may be associated to form a dimer and two units of dimer may be associated to form a tetramer. Preferably, the FRIL is in a form of a tetramer. In some embodiments, the FRIL is in a form of a tetramer arranged in a tetrahedral configuration.

In some embodiments, the FRIL is a native FRIL purified from an extract of *Lablab purpureus*. In some embodiments, the FRIL is a native FRIL purified from an aqueous extract of *Lablab purpureus*. In some embodiments, the FRIL can be recombinant which can be overexpressed from bacteria, yeast, insect cells, baculovirus, mammalian cells, or human cells.

In some embodiments, the FRIL comprises one or more carbohydrate recognition domains. In some embodiments, the FRIL binds to the coronavirus presenting appropriate surface sugars (e.g., mannose). In some embodiments, the FRIL binds to one or more glycans on the surface of the coronavirus. In some embodiments, the FRIL binds to one or more glycans on the spike (S) glycoprotein of the coronavirus.

In some embodiments, the composition described herein may further comprise a second therapeutic agent. In certain embodiments, the second therapeutic agent is selected from the group consisting of an anti-inflammatory drug, an antiviral drug, a vaccine for coronavirus, antibiotics, a dietary supplement and any other palliative therapy to treat coronavirus infection. In certain embodiments, the second therapeutic agent is an anti-viral drug. In certain embodiments, the anti-viral drug is selected from the group consisting of ribavirin, penciclovir, nitazoxanide, nafamostat, chloroquine, remdesivir (GS-5734) and favipiravir (T-705), interferon, adefovir, tenofovir, acyclovir, brivudin, cidofovir, fomivirsen, foscarnet, ganciclovir, amantadine, rimantadine and zanamivir.

The subject described herein is suffering from or susceptible to coronavirus infection, or suspected of being infected to a coronavirus. The subject may be a human or non-human organism. Preferably, the subject is a human.

The composition described herein may be formulated for administration by a route selected from the group consisting of oral, intravenous, intramuscular, intra-arterial, subcutaneous, intraventricular, transdermal, interdermal, rectal, intravaginal, intraperitoneal, topical, mucosal, nasal, buccal, enteral, sublingual, intratracheal and bronchial. In certain embodiments, the administration is by intratracheal and bronchial instillation. In certain embodiments, the composition described herein is administered by subcutaneously, intravenously, intradermally, intraperitoneally, orally, intramuscularly or intracranially. In certain embodiments, the composition described herein is formulated as an oral spray, a nasal spray, or an aerosol.

In yet another aspect, the present invention provides a pharmaceutical composition, comprising a *Lablab purpureus* FRIL, an additional therapeutic agent, and a pharmaceutically acceptable excipient. In some embodiments, the additional therapeutic agent is an anti-viral agent. In some embodiments, the anti-viral agent is selected from the group consisting of ribavirin, penciclovir, nitazoxanide, nafamostat, chloroquine, remdesivir (GS-5734) and favipiravir (T-705), interferon, adefovir, tenofovir, acyclovir, brivudin, cidofovir, fomivirsen, foscarnet, ganciclovir, amantadine, rimantadine and zanamivir.

The provided pharmaceutical composition is useful for treating or preventing a coronavirus infection. The pharmaceutical composition may also optionally be included in a device for administration of the pharmaceutical composition, for example, by oral or nasal inhalation.

In some embodiments, the present invention provides a kit comprising a composition described herein (e.g. a *Lablab purpureus* FRIL and optionally a second therapeutic agent), formulated for administration via an administration device, together with such an administration device in a set comprising one or more containers. In some embodiments, an appropriate administration device is selected from the group consisting of a syringe, needle, spray, filter, applicator, and combinations thereof. In some embodiments, a provided kit includes instructions for use.

Provided compositions and methods are useful, for example, in research and/or in medicine. In some embodiments, provided compositions and methods are useful, for example, in prophylaxis, treatment, and/or study of coronavirus.

The details of certain embodiments of the invention are set forth herein. Other features, objects, and advantages of the invention will be apparent from the Detailed Description, the Figures, the Examples, and the Claims.

BRIEF DESCRIPTION OF THE DRAWINGS

The present description will be better understood from the following detailed description read in light of the accompanying drawings, where.

DETAILED DESCRIPTION OF THE INVENTION

Figure 1:
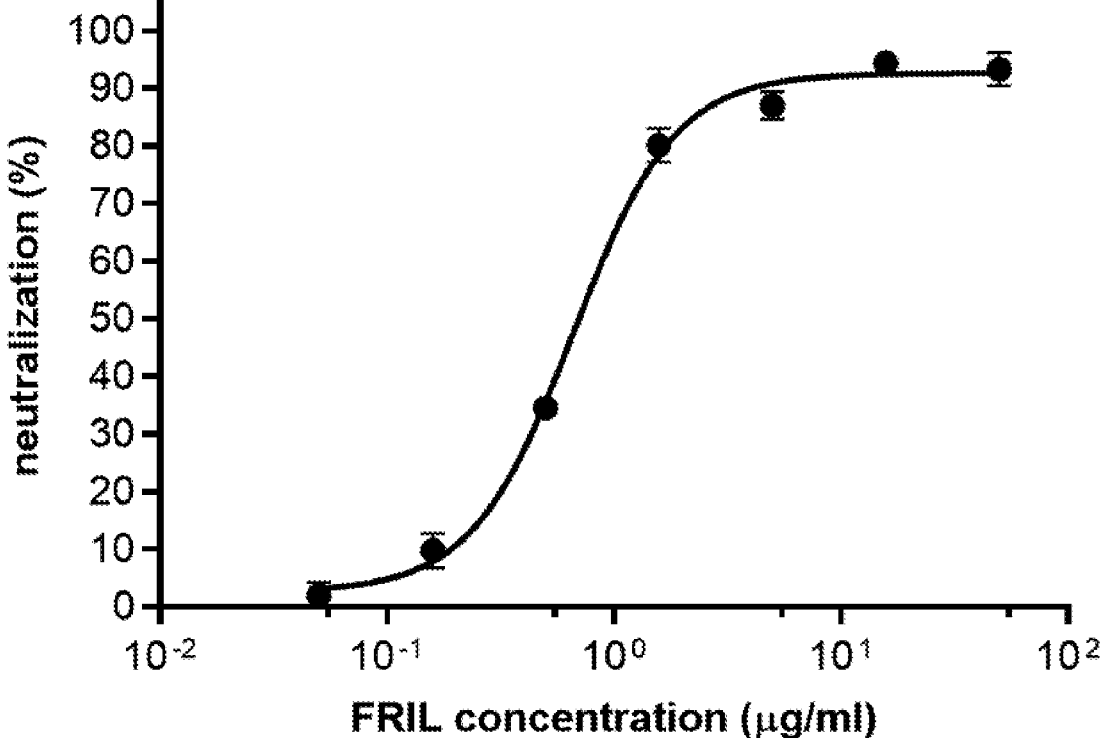
FIG. 1 shows the microneutralization titer of FRIL against SARS-CoV-2 on Vero E6 cells as detected by anti-SARS-CoV-2 N protein antibody.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, structural, functional, and other changes may be made without departing from the scope of the present disclosure. The following detailed description is, therefore, not to be taken in a limiting sense.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the term "native FRIL" means a FRIL isolated from a legume in which the protein is naturally expressed. In certain embodiments, a native FRIL is isolated from the seeds of *Lablab purpureus* in which the protein is naturally expressed.

As used herein, the term "recombinant FRIL" means a FRIL isolated from an organism in which the protein is expressed by a recombinant gene including, without limitation, bacteria, yeast, plant, or animal cells which have been transfected with a recombinant construct encoding the FRIL. A recombinant FRIL can have an amino acid sequence identical to a native FRIL, or a functional equivalent that can have an amino acid sequence including silent mutations e.g. one or more amino acid insertions, deletions, and/or substitutions including, without limitation, N-terminal additions or deletions, C-terminal additions or deletions, and chimeric proteins, without substantially changing its function.

As used herein, the term "FRIL" may refer to a native FRIL protein or recombinant FRIL protein. In certain embodiments, FRIL is a protein including about 272 amino acids. It begins with a leading sequence of 8 amino acid residues in length at the N-terminal that is normally cleaved from a mature protein. Residues 9 to appropriately 121-138 constitute an N-terminal domain (beta subunit, about 12-18 kDa) and the residues from appropriately 122-139 to 272 constitute a C-terminal domain (alpha subunit, about 12-18 kDa), wherein the residues from about 122-138 constitutes a loop domain that is proteolytic digested in various degree (completely or partially). The amino acid sequence of FRIL is as described in WO2020051397 (SEQ ID NO: 1). In certain embodiment, the amino acid residues 9-121 (SEQ ID NO: 2) constitutes the N-terminal domain (beta subunit), and the amino acid residues 139-272 (SEQ ID NO: 3) constitutes the C-terminal domain (alpha subunit), linked by loop a loop domain of amino acid residues 122-138 (SEQ ID NO: 4). In certain embodiments, the amino acid residues 1-8 (SEQ ID NO: 5) constitutes the signal peptide. In certain embodiments, the beta subunit and the alpha subunit are associated to form a monomer (αβ). In certain embodiments, two units of such monomer may be associated to form a dimer (α2β2). In certain embodiments, two units of such dimer may be associated to form a tetramer (α2β2+α2β2).

A full-length FRIL can also include those comprising an amino acid sequence which (i) are substantially identical to the amino acid sequences set forth in SEQ ID NO: 1 (for example, at least 85% (e.g., at least 90%, 95% or 97%) identical to SEQ ID NO: 1); and (ii) are encoded by a nucleic acid sequence capable of hybridizing under at least moderately stringent conditions to any nucleic acid sequence encoding the FRIL set forth herein or capable of hybridizing under at least moderately stringent conditions to any nucleic acid sequence encoding the FRIL set forth herein, but for the use of synonymous codons (e.g. a codon which does not have the identical nucleotide sequence, but which encodes the identical amino acid).

The FRIL described herein finds use in the prevention or treatment of coronavirus infection in a subject. The subject described herein is suffering from or susceptible to coronavirus infection, or suspected of being infected to a coronavirus. The subject may be a human or non-human organism. Preferably, the subject is a human. The coronavirus described herein may include SARS-CoV-2, severe acute respiratory syndrome coronavirus (SARS-CoV) and Middle East respiratory syndrome coronavirus (MERS-CoV). Preferably, the coronavirus described herein is SARS-CoV-2.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

An "effective amount" of a compound or any active ingredient as described herein of refers to an amount sufficient to elicit a desired biological response, i.e., treating the condition. As will be appreciated by those of ordinary skill in this art, the effective amount of a compound may vary depending on such factors as the desired biological endpoint, the pharmacokinetics of the compound, the condition being treated, the mode of administration, and the age and health of the subject. An effective amount encompasses therapeutic and prophylactic treatment.

The composition described herein can be mixed with a pharmaceutically acceptable carrier or excipient to form a pharmaceutical composition for use in inhibiting a coronavirus and/or treating infection caused by a coronavirus. As used herein, "inhibiting," "inhibition," "inhibit," "inhibitor," and the like, refer to the ability of an anti-coronavirus agent to reduce, slow, halt, or prevent activity of a particular biological process (e.g., coronavirus replication) in a cell relative to a control vehicle. In some instances, an anti-coronavirus agent can inhibit the level of viral replication by at least 20% (e.g., 30%, 40%, 50%, 60%, 70%, 80%, 90%, or 95%).

The term "treating" or "treatment" refers to administering one or more anti-coronavirus agent (e.g., the composition described herein) to a subject (e.g., a human patient), who has coronavirus infection, a symptom of or a predisposition toward it, with the purpose to confer a therapeutic effect, e.g., to cure, relieve, alter, affect, ameliorate, or prevent the infection, the symptom of or the predisposition toward it. Such a subject can be identified by a health care professional based on results from any suitable diagnostic method.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the anti-viral agents described herein, or more solubilizing agents, can be utilized as pharmaceutical carriers for delivery of the anti-viral agents. Examples of other carriers include colloidal silicon dioxide, magnesium stearate, sodium lauryl sulfate, and D&C Yellow # 10. See, e.g., Remington: The Science and Practice of Pharmacy, 21st Edition (Lippincott Williams & Wilkins, 2005); and Goodman and Gilman's "The Pharmacological Basis of Therapeutics", Tenth Edition, Gilman, J. Hardman and L. Limbird, eds., McGraw-Hill Press, 155-173, 2001.

Pharmaceutically acceptable excipients/carriers include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Effective amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Any of the pharmaceutical compositions described herein can be administered to a subject in need of the treatment via any conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the anti-coronavirus agent described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

A composition for oral administration can be any orally acceptable solid dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragées, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649, 912; 5,569,189; 5,704,911; 5,383,851; 5,893,397; 5,466, 220; 5,339,163; 5,312,335; 5,503,627; 5,064,413; 5,520, 639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surfactant, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

A nasal aerosol or inhalation composition can be prepared according to techniques well known in the art of pharmaceutical formulation. Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

In certain embodiments, an effective amount of an anti-coronavirus agent as described herein for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In other embodiments, the anti-coronavirus agent may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The polypeptide or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Also encompassed by the present disclosure are kits (e.g., pharmaceutical packs). The kits provided may comprise an inventive pharmaceutical composition or polypeptide and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or polypeptide. In some embodiments, the inventive pharmaceutical composition or compound provided in the container and the second container are combined to form one unit dosage form.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety for the purposes or subject matter referenced herein.

EXAMPLES

In order that the invention described herein may be more fully understood, the following examples are set forth. It should be understood that these examples are for illustrative purposes only and are not to be construed as limiting this invention in any manner.

Materials and Methods

Cells and Viruses

SARS-CoV-2 strain was isolated from a confirmed COVID-19 patient in Taiwan. The virus was propagated in Vero E6 cells that were maintained in Dulbecco's modified eagle medium (DMEM, Gibco) supplemented with 10% heat-inactivated fetal bovine serum (FBS, Gibco). The virus titers were determined in 96-well microplates with Vero E6 cells as 50% tissue culture infectious dose ($TCID_{50}$/ml) using Karber's method.

Example 1: Production of FRIL Protein From *Lablab purpureus*

FRIL protein from *Lablab purpureus* was purified according to the methods described in WO2020051397. To analyze the purified proteins, in-gel digestion was applied to collect all six bands for mass spectrometry analysis. The results confirmed the purified protein is Flt3 Receptor Interacting Lectin (FRIL).

To further purify the FRIL, sedimentation and resuspension processes were performed using 60% ammonium sulfate, followed by an affinity chromatography with mannose-sepharose beads. Next, an anion exchange with Q column starting at 150 mM NaCl was applied to deplete the non-specific bands having the MVV at 55-72 kD. The purified FRIL was collected in the flow through during the anion exchange chromatography. The yield of purified FRIL was greater than 4 mg/g bean powder.

Example 2: Assessment of Anti-SARS-CoV-2 Activity

Vero E6 cells in DMEM supplemented with 10% FBS were aliquoted into 96-well plates (100 µl/well) and incubated at 37° C. with 5% $CO_2$ for overnight to reach confluence. The cells were washed once with 100 µl of virus growth medium (DMEM with 2% FBS) per well. The medium was aspirated, and 50 µl of two-fold serially diluted FRIL, starting at 50 µg/ml, was immediately added into the medium in duplicate. Operated in P3 laboratory, 50 µl of 100 $TCID_{50}$ SARS-CoV-2 was added into each well of the 96-well plates. The 96-well plates were placed at 37° C. with 5% $CO_2$ for three days. Cytopathic morphology of the cells was then recorded and photographed by ImageXpress Nano Automated Cellular Imaging System. Each experiment was duplicated.

FIG. 1 shows the microneutralization titer of FRIL against SARS-CoV-2. FRIL and SARS-CoV-2 virus were incubated at 37° C. for 1 hour on a 96 well tissue culture plate containing $1.5 \times 10^4$ cells/well of Vero E6 cells. The plate was then cultured in serum-free media for 48 hours, and fixed with 10% formaldehyde for 24 hours. Vero E6 cells were then permeated with 0.1% Triton X, and an anti-SARS-CoV-2 N protein antibody was used to detect virus titer. An HRP-conjugated secondary antibody and a peroxidase substrate solution (TMB) were used to facilitate detection at $OD_{450}$ on an ELISA reader.

The half maximal effective concentration ($EC_{50}$) of FRIL to neutralize 100 $TCID_{50}$ of SARS-CoV-2 virus was determined to be 0.66 µg/ml using Graphpad Prism 8, corresponding to 5.89 nM (the tetrameric FRIL has a molecular weight of 112 kDa).

Example 3: Plaque Reduction Assay for SARS-CoV2

Figure 2:
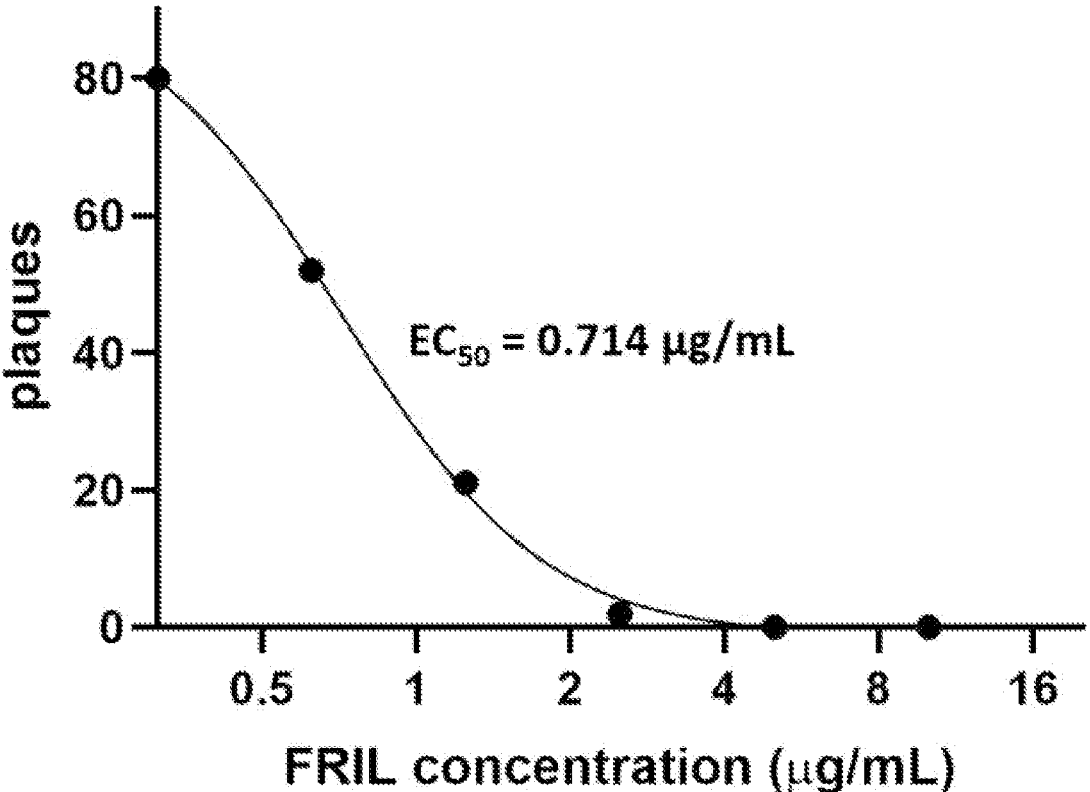
FIG. 2 shows the plaque reduction neutralization titer of FRIL against SARS-CoV-2 on Vero E6 cells with plaques visualized by crystal violet staining.

Vero E6 cells were seeded onto a 6-well plate at $2 \times 10^5$ cells/well and incubated in culture medium until 90% confluence. After confluence, the culture medium was aspirated and plates were washed twice with PBS. 200 µl of SARS-CoV-2 (100 PFU) in DMEM with 1% FBS were layered onto cells, and incubated at 37° C. for 30 minutes to facilitate virus attachment. The virus solution was then aspirated, and 0.6% low-melting agarose containing FRIL with a two-fold serially diluted concentration at 10 µg/mL, 5 µg/mL, 2.5 µg/mL, 1.25 µg/mL, 0.625 µg/mL, and 0.3125 µg/mL were layered onto individual wells. The plates were allowed to solidify at room temperature for 30 minutes, then incubated at 37° C. for 4 days or until cytopathic effects (CPE) were observed. After 4 days, cells were fixed with 10% formalin, agarose plugs were removed, and stained with 0.5% crystal violet. Plaques were plotted for further estimation. $EC_{50}$ of FRIL was determined to be 0.714 µg/mL using GraphPad Prism 8, shown in FIG. 2. The data shows that the present FRIL prevents the SARS-CoV2 infection.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

---

What is claimed is:

1. A method for treating a coronavirus infection, comprising administering to a subject in need thereof an effective amount of a composition comprising Flt3 receptor interacting lectin (FRIL) from Lablab purpureus, wherein the FRIL comprises SEQ ID NO: 1.

2. The method of claim 1, wherein the coronavirus is severe acute respiratory syndrome coronavirus-2 (SARS-COV-2) or severe acute respiratory syndrome coronavirus (SARS-COV).

3. The method of claim 1, wherein the FRIL is a native protein isolated from Lablab purpureus.

4. The method of claim 1, wherein the FRIL is a recombinant or synthetic protein.

5. The method of claim 1, wherein the FRIL is a tetrameric protein in a tetrahedral configuration.

6. The method of claim 1, wherein the FRIL comprises a region having SEQ ID NO: 2, and a region having SEQ ID NO: 3.

7. The method of claim 1, wherein the FRIL binds to one or more glycans on the coronavirus.

8. The method of claim 1, wherein the subject is suffering from or susceptible to coronavirus infection, or suspected of being infected with a coronavirus.

9. The method of claim 1, wherein the composition further comprises a second therapeutic agent.

10. The method of claim 9, wherein the second therapeutic agent is selected from the group consisting of an anti-inflammatory drug, an anti-viral drug, a vaccine for coronavirus, antibiotics, a dietary supplement and palliative therapy to treat coronavirus infection.

11. The method of claim 10, wherein the second therapeutic agent is an anti-viral drug.

12. The method of claim 11, wherein the anti-viral drug is selected from the group consisting of ribavirin, penciclovir, nitazoxanide, nafamostat, chloroquine, remdesivir (GS-5734), favipiravir (T-705), interferon, adefovir, tenofovir, acyclovir, brivudine, cidofovir, fomivirsen, foscarnet, ganciclovir, amantadine, rimantadine and zanamivir.

13. The method of claim 1, wherein the composition is administered subcutaneously, intravenously, intradermally, intraperitoneally, orally, intramuscularly or intracranially.

* * * * *

SEQUENCE LISTING

```
<160> NUMBER OF SEQ ID NOS: 5

<210> SEQ ID NO 1
<211> LENGTH: 272
<212> TYPE: PRT
<213> ORGANISM: Lablab purpureus

<400> SEQUENCE: 1

Met Phe Pro Ser Lys Val Lys Ser Ala Gln Ser Leu Ser Phe Ser Phe
1               5                   10                  15

Thr Lys Phe Asp Pro Asn Gln Glu Asp Leu Ile Phe Gln Gly His Ala
            20                  25                  30

Thr Ser Thr Asn Asn Val Leu Gln Val Thr Lys Leu Asp Ser Ala Gly
            35                  40                  45

Asn Pro Val Ser Ser Ser Ala Gly Arg Val Leu Tyr Ser Ala Pro Leu
        50                  55                  60

Arg Leu Trp Glu Asp Ser Ala Val Leu Thr Ser Phe Asp Thr Ile Ile
65                  70                  75                  80

Asn Phe Glu Ile Ser Thr Pro Tyr Thr Ser Arg Ile Ala Asp Gly Leu
                85                  90                  95

Ala Phe Phe Ile Ala Pro Pro Asp Ser Val Ile Ser Tyr His Gly Gly
            100                 105                 110

Phe Leu Gly Leu Phe Pro Asn Ala Asn Thr Leu Asn Asn Ser Ser Thr
        115                 120                 125

Ser Glu Asn Gln Thr Thr Thr Lys Ala Ala Ser Ser Asn Val Val Ala
        130                 135                 140

Val Glu Phe Asp Thr Tyr Leu Asn Pro Asp Tyr Gly Asp Pro Asn Tyr
145                 150                 155                 160

Ile His Ile Gly Ile Asp Val Asn Ser Ile Arg Ser Lys Val Thr Ala
                165                 170                 175

Lys Trp Asp Trp Gln Asn Gly Lys Ile Ala Thr Ala His Ile Ser Tyr
            180                 185                 190

Asn Ser Val Ser Lys Arg Leu Ser Val Thr Ser Tyr Tyr Ala Gly Ser
        195                 200                 205

Lys Pro Ala Thr Leu Ser Tyr Asp Ile Glu Leu His Thr Val Leu Pro
        210                 215                 220

Glu Trp Val Arg Val Gly Leu Ser Ala Ser Thr Gly Gln Asp Lys Glu
225                 230                 235                 240

Arg Asn Thr Val His Ser Trp Ser Phe Thr Ser Ser Leu Trp Thr Asn
                245                 250                 255

Val Ala Lys Lys Glu Asn Glu Asn Lys Tyr Ile Thr Arg Gly Val Leu
                260                 265                 270

<210> SEQ ID NO 2
<211> LENGTH: 113
<212> TYPE: PRT
<213> ORGANISM: Artificial Sequence
```

```
<220> FEATURE:
<223> OTHER INFORMATION: beta subunit

<400> SEQUENCE: 2

Ala Gln Ser Leu Ser Phe Ser Phe Thr Lys Phe Asp Pro Asn Gln Glu
1               5                   10                  15

Asp Leu Ile Phe Gln Gly His Ala Thr Ser Thr Asn Asn Val Leu Gln
                20                  25                  30

Val Thr Lys Leu Asp Ser Ala Gly Asn Pro Val Ser Ser Ser Ala Gly
            35                  40                  45

Arg Val Leu Tyr Ser Ala Pro Leu Arg Leu Trp Glu Asp Ser Ala Val
        50                  55                  60

Leu Thr Ser Phe Asp Thr Ile Ile Asn Phe Glu Ile Ser Thr Pro Tyr
65                  70                  75                  80

Thr Ser Arg Ile Ala Asp Gly Leu Ala Phe Phe Ile Ala Pro Pro Asp
                85                  90                  95

Ser Val Ile Ser Tyr His Gly Gly Phe Leu Gly Leu Phe Pro Asn Ala
                100                 105                 110

Asn

<210> SEQ ID NO 3
<211> LENGTH: 134
<212> TYPE: PRT
<213> ORGANISM: Artificial Sequence
<220> FEATURE:
<223> OTHER INFORMATION: alpha subunit

<400> SEQUENCE: 3

Ser Ser Asn Val Val Ala Val Glu Phe Asp Thr Tyr Leu Asn Pro Asp
1               5                   10                  15

Tyr Gly Asp Pro Asn Tyr Ile His Ile Gly Ile Asp Val Asn Ser Ile
                20                  25                  30

Arg Ser Lys Val Thr Ala Lys Trp Asp Trp Gln Asn Gly Lys Ile Ala
            35                  40                  45

Thr Ala His Ile Ser Tyr Asn Ser Val Ser Lys Arg Leu Ser Val Thr
        50                  55                  60

Ser Tyr Tyr Ala Gly Ser Lys Pro Ala Thr Leu Ser Tyr Asp Ile Glu
65                  70                  75                  80

Leu His Thr Val Leu Pro Glu Trp Val Arg Val Gly Leu Ser Ala Ser
                85                  90                  95

Thr Gly Gln Asp Lys Glu Arg Asn Thr Val His Ser Trp Ser Phe Thr
                100                 105                 110

Ser Ser Leu Trp Thr Asn Val Ala Lys Lys Glu Asn Glu Asn Lys Tyr
            115                 120                 125

Ile Thr Arg Gly Val Leu
        130

<210> SEQ ID NO 4
<211> LENGTH: 17
<212> TYPE: PRT
<213> ORGANISM: Artificial Sequence
<220> FEATURE:
<223> OTHER INFORMATION: Loop domain

<400> SEQUENCE: 4

Thr Leu Asn Asn Ser Ser Thr Ser Glu Asn Gln Thr Thr Thr Lys Ala
1               5                   10                  15

Ala
```

-continued

```
<210> SEQ ID NO 5
<211> LENGTH: 8
<212> TYPE: PRT
<213> ORGANISM: Artificial Sequence
<220> FEATURE:
<223> OTHER INFORMATION: Signal peptide

<400> SEQUENCE: 5

Met Phe Pro Ser Lys Val Lys Ser
1               5
```